United States Patent
Warren et al.

(10) Patent No.: US 7,368,291 B2
(45) Date of Patent: May 6, 2008

(54) SULFURYL FLUORIDE FUMIGATION PROCESS

(75) Inventors: Malcolm Wayne Warren, Midland, MI (US); James Lawrence Witt, Tampa, FL (US)

(73) Assignee: Dow AgroSciences LLC, Indianapolis, IN (US)

( * ) Notice: Subject to any disclaimer, the term of this patent is extended or adjusted under 35 U.S.C. 154(b) by 894 days.

(21) Appl. No.: 10/478,708

(22) PCT Filed: May 31, 2002

(86) PCT No.: PCT/US02/17002

§ 371 (c)(1),
(2), (4) Date: Jan. 12, 2004

(87) PCT Pub. No.: WO02/097430

PCT Pub. Date: Dec. 5, 2002

(65) Prior Publication Data

US 2004/0137636 A1    Jul. 15, 2004

(51) Int. Cl.
    *G01N 33/00* (2006.01)
    *G01N 25/56* (2006.01)
    *B32B 5/02* (2006.01)

(52) U.S. Cl. ............... 436/120; 436/119; 436/147; 73/25.04; 73/25.3; 73/29.01; 422/83

(58) Field of Classification Search .............. None
See application file for complete search history.

(56) References Cited

U.S. PATENT DOCUMENTS

| 4,950,464 A | 8/1990 | Fujioka et al. | 423/468 |
| 5,824,919 A * | 10/1998 | Hansen | 73/863.23 |
| 5,996,397 A | 12/1999 | Mettes | 73/29.01 |

OTHER PUBLICATIONS

Fumiscope Version 5.0 Operating instructions (Oct. 2001); http://www.fumiscope.com/manual.htm.*
Cerification Training Manual for the Structural Pesticide Applicator (CTMSPA), published around 1975, pp. 123-140.*
Ping et al. "Concentration of inorganic acids by pervaporation", Recent Progress en Genie des Procedes, 1992, 6 (21), pp. 325-329, Abstract.*
PCT/US02/17002; Written opinion; Mar. 24, 2003.*
Miyoshi, et al., "Pervaporation of Water-Carboyxlic Acid Solution with Ion Exchange Membranes", Maku, 1988, v. 13, No. 2, pp. 109-115.

* cited by examiner

Primary Examiner—Yelena G. Gakh
(74) Attorney, Agent, or Firm—Carl Corvin

(57) ABSTRACT

A process is provided for determining the amount of sulfuryl fluoride in the atmosphere of an enclosed area that has been fumigated with sulfuryl fluoride ($SO_2F_2$). This process comprises: (A) sampling said atmosphere of said enclosed area to obtain a gaseous sample; (B) selectively removing water from said gaseous sample by passing said gaseous sample through a perevaporation zone to obtain a perevaporated sample, wherein said perevaporation zone comprises a copolymer of tetrafluoroethylene and perfluoro-3,6-dioxa-4-methyl-7-octene-sulfonic acid; and (C) analyzing said perevaporated sample in a sulfuryl fluoride detector to determine the amount of sulfuryl fluoride in said perevaporated sample.

3 Claims, No Drawings

SULFURYL FLUORIDE FUMIGATION PROCESS

BACKGROUND OF THE INVENTION

This invention is related to the field of fumigation processes that use sulfuryl fluoride as a fumigant.

It is well known that insects and other pests are very destructive to property and that they can endanger human life. It has been estimated that termites alone cause more than 750 million dollars in damage every year, much of this damage is done to homes where families live.

Fumigation is the use of certain gases to control insects and other pests that are present in enclosed, or enclosable, areas where they are not desired, such as, family homes. Currently, the fumigant of choice is sulfuryl fluoride. The preferred source for sulfuryl fluoride is Dow AgroSciences LLC., which sells a specialty sulfuryl fluoride product under the trademark Vikane® gas fumigant.

During fumigation it is important to know the amount of sulfuryl fluoride in the air of the enclosed area. This is because a certain level of sulfuryl fluoride is needed in the air of the enclosed area in order to rid such area of the insects and other pests that are present therein. Consequently, a Fumiscope is used to determine this amount.

A Fumiscope is a portable instrument that will quantitatively measure the gas concentration in air by sampling the atmosphere of the enclosed area. However: there are certain problems with using a Fumiscope. In particular, most, if not all, Fumiscopes that measure sulfuryl fluoride are sensitive to the amount of water vapor in the air. That is, the amount of water vapor adversely affects the detection capabilities of the Fumiscope. One preferred method to overcome this problem is to use a drying material such as, anhydrous calcium sulfate to absorb the water vapor. However, this solution is not optimal. First, these types of dryers can remove other gases, such as sulfuryl fluoride, from the sample thereby making the Fumiscope give an inaccurate reading. Second, these types of dryers are used up during the monitoring, and consequently, the effectiveness of these dryers decreases over time and the baseline of the Fumiscope drifts. This means that the dryers must be replaced often during monitoring and the Fumiscope must be re-zeroed during monitoring in order to get accurate readings. These procedures are time consuming and labor-intensive and prevent the unattended operation of the Fumiscope.

Consequently, in light of the above the inventors provide the following solution to this problem.

BRIEF SUMMARY OF THE INVENTION

It is an object of this invention to provide a sulfuryl fluoride fumigation process.

In accordance with this invention a process is provided for determining the amount of sulfuryl fluoride in the atmosphere of an enclosed area that has been fumigated with sulfuryl fluoride ($SO_2F_2$). This process comprises:
(A) sampling said atmosphere of said enclosed area to obtain a gaseous sample;
(B) selectively removing water from said gaseous sample by passing said gaseous sample through a perevaporation zone to obtain a perevaporated sample, wherein said perevaporation zone comprises a copolymer of tetrafluoroethylene and perfluoro-3,6-dioxa-4-methyl-7-octene-sulfonic acid; and
(C) analyzing said perevaporated sample in a sulfuryl fluoride detector to determine the amount of sulfuryl fluoride in said perevaporated sample.

Additional information on this invention is provided in detail in the following.

DETAILED DESCRIPTION OF THE INVENTION

Fumigation is well known in the art. It can be conducted in any area that is enclosed or enclosable. Specific examples are homes, office buildings, and churches. For the purposes of this invention, the fumigant of choice is sulfuryl fluoride ($SO_2F_2$).

The first step in this invention is to sample the atmosphere of the sulfuryl-fluoride-fumigated-enclosed area to obtain a gaseous sample. This sampling can be conducted continuously or intermittently at the discretion of the licensed fumigation operator.

The second step in the process is to selectively remove water from the gaseous sample. This is accomplished by passing the gaseous sample through a perevaporation zone. This produces a perevaporated sample. The perevaporation zone comprises a membrane made from a copolymer of tetrafluoroethylene and perfluoro-3,6-dioxa-4-methyl-7-octene-sulfonic acid. Currently, it is preferred to use Nafion® copolymer because it is highly selective in the removal of water from gases (Nafion® is a registered trademark of E.I. DuPont). The sole supplier of Nafion tubing to the world is PermaPure Inc which has a web site at www.permapure.com. As the sample moves through the perevaporation zone, water is selectively removed from the sample. The water, so removed, then passes through the membrane wall of the copolymer where it evaporates into the surrounding air.

The third step of the process is to analyze said perevaporated sample in a sulfuryl fluoride detector to determine the amount of sulfuryl fluoride in said perevaporated sample. This analysis is conducted by a sulfuryl fluoride detector that is sensitive to the presence of water in the gaseous sample. One example of a sulfuryl fluoride detector is a Fumiscope. One can obtain a Fumiscope that performs sulfuryl fluoride detection from Key Chemical & Equipment Co. Inc., 13195 49th Street North Unit A, Clearwater, Fla. 33762 USA. After the amount of sulfuryl fluoride is determined, this value can be used to determine if a sufficient quantity of sulfuryl fluoride is present in the air so that the enclosed area is properly fumigated.

During testing of a Fumiscope using a standard drying tube comprising anhydrous calcium sulfate and one using a Nafion drying tube the results were extraordinary. The Fumiscope with the standard drying tube required changing of the drying tube and constant re-zeroing of the Fumiscope in order to take accurate readings. On the other hand, the Fumiscope that used the Nafion tubing, which pulled the sample through the tubing before passing the perevaporated sample into the detector ran for weeks with no drift and no need to re-zero the instrument.

Additional side-by-side laboratory testing showed that a Fumiscope using a standard drying tube comprising anhydrous calcium sulfate took longer to achieve the correct reading and took longer to re-zero than the Fumiscope equipped with a Nafion drying tube.

Consequently, this invention gives more accurate readings and it provides these reading quicker, and with less re-zeroing than the industry standard.

We claim:

1. A process for determining the amount of sulfuryl fluoride in the atmosphere of an enclosed area that has been fumigated with sulfuryl fluoride ($SO_2F_2$) this process comprises:
(A) sampling said atmosphere of said enclosed area to obtain a gaseous sample;
(B) selectively removing water from said gaseous sample by passing said gaseous sample through a perevaporation zone to obtain a perevaporated sample, wherein said perevaporation zone comprises a copolymer of tetrafluoroethylene and perfluoro-3,6-dioxa-4-methyl-7-octene-sulfonic acid; and (C) analyzing said perevaporated sample in a sulfuryl fluoride detector to determine the amount of sulfuryl fluoride in said perevaporated sample.

2. A process comprising fumigating an enclosed area with sulfuryl fluoride ($SO_2F_2$) and then determining the concentration of sulfuryl fluoride ($SO_2F_2$) using a Fumiscope equipped with a perevaporation zone that comprises a copolymer of tetrafluoroethylene and perfluoro-3,6-dioxa-4-methyl-7-octene-sulfonic acid.

3. A Fumiscope equipped with a perevaporation zone that comprises a copolymer of tetrafluoroethylene and perfluoro-3,6-dioxa-4-methyl-7-octene-sulfonic acid.

* * * * *